United States Patent [19]

Barabino et al.

[11] Patent Number: 4,799,815
[45] Date of Patent: Jan. 24, 1989

[54] LIQUID DISPENSING SWAB APPLICATOR SYSTEM

[75] Inventors: William A. Barabino, North Reading; Raymond S. Dean, Lynn, both of Mass.

[73] Assignee: Triad Direct Incorporated, Placentia, Calif.

[21] Appl. No.: 85,771

[22] Filed: Aug. 17, 1987

[51] Int. Cl.⁴ .............................................. A61M 35/00
[52] U.S. Cl. ................................... 401/132; 401/134; 401/135; 604/3
[58] Field of Search ............... 401/139, 138, 132, 133, 401/134, 137, 135; 604/3, 2, 1

[56] References Cited

U.S. PATENT DOCUMENTS

| | | | |
|---|---|---|---|
| 362,056 | 5/1887 | Block | 401/137 |
| 1,132,449 | 3/1915 | Cox | 401/139 |
| 2,333,070 | 10/1943 | Hoey et al. | |
| 3,757,782 | 9/1973 | Aiken | 401/132 X |
| 3,774,609 | 11/1973 | Schwartzman | 401/134 X |
| 3,958,571 | 5/1976 | Bennington | 604/3 |
| 4,173,978 | 11/1979 | Brown | |
| 4,740,194 | 4/1988 | Barabino | |

Primary Examiner—Steven A. Bratlie
Attorney, Agent, or Firm—Richard C. Litman

[57] ABSTRACT

A liquid dispensing swab applicator for dispensing a liquid contained within the applicator onto a surface, the applicator being hermetically sealed and provided with an external jig for opening the sealed applicator and permitting the contents of the applicator to be discharged and supplied to an absorbent material attached to the end of the applicator, the absorbent material serving to apply the contents to the surface to be treated.

2 Claims, 1 Drawing Sheet

LIQUID DISPENSING SWAB APPLICATOR SYSTEM

BACKGROUND TO THE INVENTION

The present invention relates to a swab applicator system having no self-provided means for liquid removal, but which is subsequently used to apply liquid to a surface and particularly to a swab applicator in which the liquid to be applied is contained within the shaft of the swab and dispensed from the shaft to an absorbent tip, which is used to apply the liquid on a surface. A separate tool or jig is provided to access the contents of the applicator shaft and enable it to be dispensed onto the swab surface.

Cotton tipped swabs find wide applications, particularly in the medical field where they are used to apply topical antiseptics, cleanse skin surfaces, remove cerumen from the ears and in many other ways. Swab applicators also find wide industrial uses in the cleaning of surfaces and the point placement of solvents and lubricants. In most of these uses, the cotton tipped swab is used with an externally supplied liquid such as an antiseptic or a solvent and its use requires that the swab be dipped and redipped into the liquid during the application or cleaning process. This redipping of the swab in the reservoir of supply liquid may result in the contamination of the liquid by foreign particles or spore forming bacteria being transferred from the surface to the swab in cotton form and then to the liquid.

The present invention discloses a swab applicator which carries its own supply of working liquid sealed within its shaft and externally dispenses its working liquid from the shaft of the swab onto its absorbent cotton form for application to a surface. The supply of working liquid within the shaft of the swab eliminates the need for redipping the swab into a central liquid supply, thereby preventing contamination of a bottle of antiseptic or cleaning fluid by repeated dipping, application, and re-dipping of the swab from a surface to the supply liquid reservoir.

The present invention also presents a liquid dispensing swab application system having its own self-contained liquid supply, but having no self-providing means to dispense its contents. It requires the use of an external fixture or tool to release the contents of the fluid reservoir to the absorbent tip. This safety feature reduces the probability that the applicator will be abused by a child.

DESCRIPTION OF THE PRIOR ART

While various swab applicators have been shown in the prior patent art, they have principally been concerned with ampoules of crushable glass which dispense antiseptics or inhalants. Such applicators are discussed in Hoey, U.S. Pat. No. 2,333,070, Aiken, U.S. Pat. No. 3,757,782, Truhan, U.S. Pat. No. 3,759,259 and Brown, U.S. Pat. No. 4,173,978. Bennington in U.S. Pat. No. 3,958,259 discloses an open-ended swab which does not provide any protection against evaporation or loss of contents. The swab in our co-pending application ser. No. 905,967, now U.S. Pat. No. 4,740,194 issued Apr. 26, 1988, discloses a self-contained liquid swab application and method for its manufacture, wherein a method is shown for the insertion of air separated liquid segments in extraordinary lengths of tubing. Stated alternately, the liquid dispensing swab as described herein is not singularly filled.

SUMMARY OF THE INVENTION

The present invention provides a swab applicator in which the shaft of the swab is formed of a hollow tubing which contains the working liquid to be applied from the shaft to a cotton tip, and from the cotton tip to a surface to be treated or coated with the liquid. The hollow tubing forming the reservoir for the working liquid is hermetically sealed at both ends, and the working liquid is centrally positioned within the shaft, providing an air space at each end of the tube. Methods have been disclosed, such as in our above-mentioned patent, describing singularly filled liquid dispensing swabs; wherein individual manufactures may economically produce the hermetically sealed tubing. A cotton form or other absorbent material is provided at one or both ends of the sealed shaft. The use of a highly flexible material for the tubing such as polypropylene permits flexing or abuse of the shaft by a child without releasing the contents of the reservoir. A single and separate fixture or jig is provided for use with the swab which are manually packaged in consumer quantities, the fixture serving to puncture the tube adjacent to the cotton form for dispensing the contents from the shaft to the cotton form and to provide a vent hole at the opposite end of the shaft. This permits the dispensing of liquid contents having a high viscosity and which may otherwise be difficult to squeeze from the tube. When employed with low viscosity liquids, single orifice is required. The dispersion of the liquid is controlled by gently squeezing the tube. When the shaft is punctured, the liquid will be wicked onto the absorbent surface of the cotton form by gently squeezing the tube until the desired amount of liquid is dispensed. After a first use, the cotton form may be resupplied with liquid from the shaft until the operation is completed or the shaft is depleted. The swab applicator is then disposed and, if further applications are required, a new applicator or applicators are used to complete the procedure.

DESCRIPTION OF THE PREFERRED EMBODIMENTS

Figure 1:
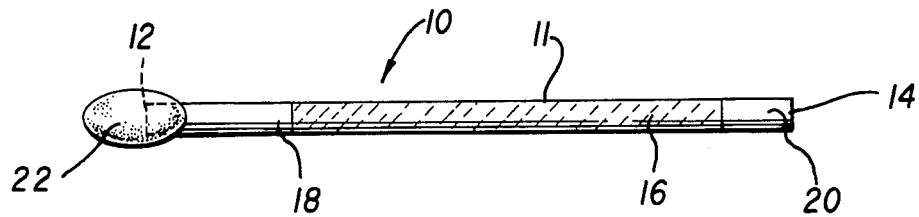
FIG. 1 is a side view of the swab applicator.

Referring now to the drawings in which like numbers are used to describe like parts, there is shown in FIG. 1 a swab applicator 10 which is constructed of a tubular plastic material 11 such as polypropylene although other plastics may be used to provide compatability with the contents. The tubing diameter and length are selected as a function of the amount and viscosity of the liquid to be contained and dispensed from the tube. Tubing 11 is filled with a fluid 16 leaving an air space 18 and 20 at each end thereof. Tube material 11 is sealed at each end by hermetic seals 12 and 14 which may be heat sealed or welded, depending upon the plastic tubing employed. An absorbent tip 22 is provided at one end of the shaft 10 for applying the dispensed contents of the shaft to the surface to be treated. Absorbent tip 22 may be cotton or any other absorbent material which will retain the dispensed liquid and enable it to be applied to a working surface such as the skin or an industrial electronic component.

In the configuration shown in FIG. 1, the swab applicator is a closed system having no self-provided means for dispensing its liquid content and highly resistant to abuse or misuse by children. The use of a flexible material for the shaft disallows release of the liquid by inadvertent flexure. The swab applicator system requires the use of an external jig or fixture in order to puncture the tubing to enable the release of the liquid from the shaft to the absorbent tip.

Figure 3B:
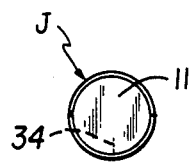
FIGS. 3A and 3B show an end view of the swab, within the semicylindrical structure, prior to the swab being punctured, and after the swab has been punctured, respectively.
Figure 2:
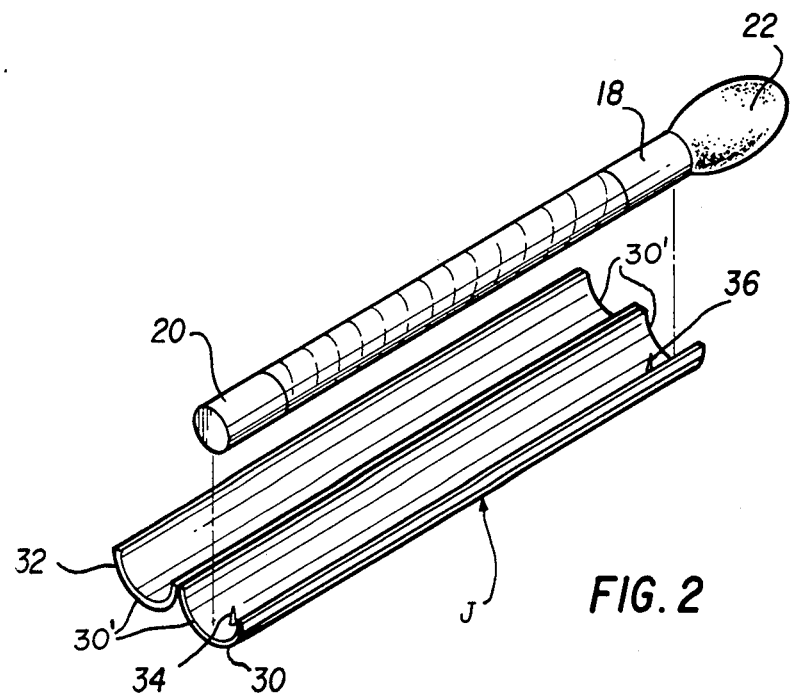
FIGS. 2 is a perspective view of the applicator puncture jig with the swab applicator ready for puncture.

Release means, in the form of an applicator puncture jig J is shown in FIG. 2. The puncture jig comprises a semicylindrical member 30 having a self-hinged, semicylindrical cover 32 attached thereto, which, when closed, provides a fitted fully encircling enclosure for the swab applicator as shown in FIG. 3B. Puncture tips 34 and 36 are provided adjacent each end 30 of the semicylindrical member 30 and are spaced within the member 30 so that when the swab shaft is placed in the puncture jig and its cover 32 closed, from the position of FIG. 3A to that of FIG. 3B, the puncture tips 34 and 36 puncture the air space 18 forming a liquid exit orifice and airspace 20 forming a back pressure relief (or vent) orifice at the respective ends of the swab applicator shaft 11 so that the liquid 16 may be dispensed from the shaft to the absorbent tip 22, by migration upon the periphery of the shaft. The diameters of the puncture tips are universal. However, a smaller puncture tip can be used for the vent puncture, while a larger puncture tip can be provided for the dispensing puncture.

Figure 3A:
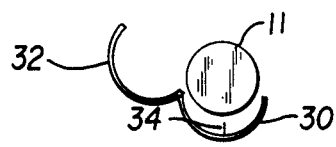

FIG. 3A shows an end view of the swab, 10 within the semicylindrical member 30 prior to the closure and the puncture of the swab 10.

FIG. 3B shows the piercing operation as the cover 32 of the puncture jig is closed over the other member 30 of the jig 30 having the puncture points 34 and 36 with the swab shaft enclosed therein. Finger pressure applied at the top ends of the jig members 30 and 32 will cause the puncture tips 34 and 36 to perforate the swab shaft in the areas of the air spaces 18, 20. This closed construction of the puncture jig prevents inadvertent injury to the user which could be caused by overenthusiastic application of force to a tube, having a jig without the cover member. The use of the jig also prevents injury to the user which might be caused by using external puncturing members, such as needles, in an attempt to puncture the tubing at the correct points.

Figure 4:
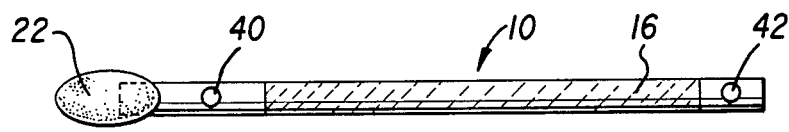
FIG. 4 is a view of the applicator ready for use with release and vent holes punched.

In FIG. 4, there is shown the swab ready for use. Holes 40 and 42 have been pierced in the tube 11 by the piercing jig and a light squeeze on the flexible plastic shaft will cause the liquid to exit from the shaft through the opening 40 to the absorbent material. Hole 40 is located immediately behind and adjacent to the absorbent surface 22 so that the amount of liquid supplied to the tip can be precisely controlled by the user. For cleaning operations, the user may want the swab tip to be saturated; while for a topical application of antiseptic or a medicament, a lesser amount of liquid may be desired. Previous devices, which disclosed the fluid contained therein as being dispensed within the absorbent material, did not permit this closely observable control of the saturation of the cotton form.

What is claimed is:

1. A liquid dispensing swab applicator system for dispensing a liquid to a surface comprising:
   a hollow applicator shaft containing a liquid therein,
   said shaft having two ends hermetically sealed and bounding a medial area,
   said liquid normally separated from both said ends and retained within the medial area of said shaft by respective air pockets within said shaft adjacent said two ends,
   an absorbent tip mounted upon one said end of said shaft for externally receiving said liquid contained within said shaft,
   elongated release means comprising a pair of hingedly joined substantially curved members having opposite ends linearly spaced apart a distance no less than the distance between said air pockets,
   a puncturing element adjacent each said end of one said release means member, and
   said pair of release members surroundable about said shaft with said puncturing elements juxtaposed those portions of said shaft ends containing said air pockets, whereby
   closing of said pair of release members with said shaft therebetween simultaneously forces said puncturing elements to pierce said shaft to provide openings therethrough to permit said liquid to migrate upon the external periphery of said shaft to said absorbent tip.

2. A liquid dispensing swab applicator system according to claim 1 wherein,
   said release members each comprise substantially semicircular elements.

* * * * *